United States Patent [19]

Marcus et al.

[11] Patent Number: 4,986,280
[45] Date of Patent: Jan. 22, 1991

[54] HAND POSITION/MEASUREMENT CONTROL SYSTEM

[75] Inventors: Beth Marcus, Lexington; W. Thompson Lawrence, Bedford; Philip Churchill, Arlington, all of Mass.

[73] Assignee: Arthur D. Little, Inc., Cambridge, Mass.

[21] Appl. No.: 222,092

[22] Filed: Jul. 20, 1988

[51] Int. Cl.⁵ .............................. A61B 5/103
[52] U.S. Cl. .......................... 128/774; 128/782; 33/512
[58] Field of Search .................... 128/774, 782; 33/511–515, 504, 534; 269/322–326, 328

[56] References Cited

U.S. PATENT DOCUMENTS

| | | |
|---|---|---|
| 1,590,499 | 6/1926 | Cozad. |
| 3,258,007 | 6/1966 | Karpovich et al. |
| 3,364,929 | 1/1968 | Ide et al. ............... 128/782 |
| 3,717,857 | 2/1973 | Evans ................. 340/177 R |
| 3,786,458 | 1/1974 | Horner et al. .......... 340/196 |
| 4,037,480 | 7/1977 | Wagner ................ 73/432 R |
| 4,046,262 | 9/1977 | Vykukal et al. ......... 214/1 CM |
| 4,328,621 | 5/1982 | Benjamin .............. 33/174 L |
| 4,436,099 | 3/1984 | Raftopoulos ........... 128/782 |
| 4,444,205 | 4/1984 | Jackson ............... 128/782 |
| 4,534,694 | 8/1985 | Tuda .................. 414/735 |
| 4,608,525 | 8/1986 | Mori et al. ........... 318/568 |
| 4,667,685 | 5/1987 | Fine .................. 128/782 |
| 4,674,048 | 6/1987 | Okumura .............. 364/424 |
| 4,834,057 | 5/1989 | McLeod, Jr. ........... 128/782 |

FOREIGN PATENT DOCUMENTS

| | | | |
|---|---|---|---|
| 231711 | 11/1968 | U.S.S.R. ........... | 128/782 |
| 0997674 | 2/1983 | U.S.S.R. ........... | 128/782 |

OTHER PUBLICATIONS

Townsend et al., "Total Motion Knee Goniometry", 1977.
Foley, James D., Interfaces for Advanced Computing, *Scientific American*, Oct. 1987, pp. 127–135.

*Primary Examiner*—Max Hindenburg
*Assistant Examiner*—John P. Lacyk
*Attorney, Agent, or Firm*—Schiller, Pandiscio & Kusmer

[57] ABSTRACT

A system is described for sensing the relative angular orientation of two relatively movable joint segments of a living body joined together at a joint. The system comprises at least two links coupled together about a pivot axis so that the links are pivotable relative to one another about the axis so as to define a variable mechanical angle between the links about the axis. The two links are secured respectively to the joint segments so that the links pivot about the pivot axis when the joint segments pivot about said joint. A Hall effect sensor is used to accurate sense the mechanical angle. The mechanical angle sensed by the sensor is then correlated with the actual angle made by the joint segments. The arrangement is used with each finger and thumb joint of the hand to provide data representative of finger and thumb orientations of a hand.

22 Claims, 6 Drawing Sheets

HAND POSITION/MEASUREMENT CONTROL SYSTEM

The present invention relates generally to a system for measuring the relative angular orientation of two relatively movable skeletal links or segments of a living body joined together at a joint, and more specifically to an improved, input device for generating signals representative of the relative angles of the finger and thumb links of the hand.

Devices and systems are well known for measuring or monitoring one or more characteristics of an anatomical part (see for example, U.S. Pat. Nos. 3,258,007 and 3,364,929), and specifically, a human joint (see, for example, U.S. Pat. Nos. 1,590,499; 3,717,857; 3,786,458; 4,037,480; 4,046,262; 4,436,099; 4,444,205; and 4,667,685). A human controlled position sensing device for use in the field of robotics is also well known (see, for example, U.S. Pat. Nos. 4,328,621; 4,534,694; 4,608,525; and 4,674,048).

The present invention generally relates to such a system and is specifically adapted to have at least two applications. The system is useful in measuring the angle between two skeletal links so that the system can be used to measure joint range of motion. It is also useful in generating electrical signals representative of various positions of an anatomical part, most notably the hand, so that the positions can be replicated for control of a robot.

At least two systems, adapted to be worn on the operator's hand for generating electrical signals representative of hand position, recently have been proposed. Generally, each of these systems includes a plurality of sensors for sensing movements of various parts of the hand. The outputs of the sensors are used to provide various electrical signals representative of the position of various parts of the hand. For example, one such system, which is currently commercially available, is the DATAGLOVE MODEL 2 SYSTEM sold by VPL Research Inc. of Redwood City, CA. This system includes various sensors secured to a glove. The user wears the glove so that as he or she moves each finger and thumb, the sensors generate signals representative of the hand gestures. While the glove provides limited stretching to conform to the size and shape of the user's hand, the sensed movements may not be very accurate. The sensors are secured to the glove so that movement between the hand and glove (and thus the sensors) will create motion artifacts and thus errors in the signals generated by the sensors. Such motion artifacts tend to occur during normal motions of the hand for two reasons. Firstly, the glove does not securely affix the sensors to the hand due to fit problems. Secondly, the fingers and thumb actually may change shape (i.e., each segment may change in its cross-sectional dimension) as the fingers and thumb are moved.

An exoskeletal sensor unit has been developed by Sarcos, Inc. of Salt Lake City, UT. The Sarcos unit utilizes links secured to the segments of each finger and thumb. A pair of links are rigidly secured to adjacent finger segments forming each joint (including each knuckle). Each pair of links are joined about a pivot axis, above the finger joint so that the two links pivot when the finger segments are pivoted about the finger joint. A potentiometer is used at the pivot axis for sensing relative angular movement between the links and for generating a signal representative of the angle between the two links (in a similar manner to the devices shown in U.S. Pat. Nos. 3,258,007; 4,046,262; 4,667,685). The signal is applied directly to a robotic hand for controlling the angular orientation of corresponding joint segments of the robotic hand.

While this prior art system helps reduce motion artifacts inherent in the glove type system, this exoskeletal sensor system cannot provide accurate measurements and/or control signals. The angle sensed by the potentiometer is a function of both the angular movement of the particular joint to which the corresponding links are attached, the geometry and dimensions of the links and hand, and the manner in which the sensor unit is attached to the hand. Additionally, the exoskeletal unit is bulky and difficult to wear. The individual links are rigidly secured to the finger and thumb segments so that the construction assumes each finger and thumb is straight and that, when bent, the pivot axes of all the joints remain parallel throughout the range of motion. Neither assumption is usually correct since the long axis of a person's finger can be and is often bent so that the finger may twist as it bends causing the axes of the various finger joints to move in a non-parallel fashion. Further, under such circumstance, with the exoskeleton unit being secured to solid blocks which are not contoured to adapt to different finger sizes and each block being secured with an elastic band to the fingers and thumb of the hand, as the fingers and thumb are bent, motion artifacts are introduced because of relative movement between the hand and the exoskeletal unit attributed to stretching of the elastic strap in different directions and rocking of the block on the finger as a result of the hand movement.

Accordingly, it is a general object of the present invention to provide an improved system for measuring the angular orientation at a movable joint of a living body, which unit substantially reduces or overcomes the foregoing problems.

A more specific object of the present invention is to provide an improved system for measuring the angular orientation at a movable joint of a living body with improved accuracy and greater resolution, while minimizing errors attributed to motion artifacts.

Another specific object of the present invention is to provide an improved system for measuring the relative angle between a pair of links secured to joint segments forming a movable joint of a living body, and correlating the measurement with the geometry of the mechanical system and the particular joint to which the links are used.

And another specific object of the present invention is to provide an improved system for measuring movement of the fingers of a hand and adapted to calibrate the angular measurements made by the system with the corresponding angular measurements of the joints of the fingers.

Yet another object of the present invention is to provide an improved exoskeletal system for sensing the angular movement of the fingers, the unit being light weight, comfortable to wear and adapted to conform to any size hand and various finger movements.

These and other objects of the present invention are achieved by an improved system for sensing the relative angular orientation of two movable adjacent joint link segments of a living body joined together at a joint. The system comprises:

first and second links coupled together about a pivot axis so that said link segments are pivotable relative to one another about said axis so as to define a variable angle between said segments about said axis;

means for securing said first and second link segments respectively to said joint segments so that said link segments pivot about said pivot axis when said joint segments pivot about said joint;

sensor means, secured to said first and second link segments, for sensing said mechanical angle; and means for correlating the mechanical angle sensed by said sensor means with the angle made by said joint segments.

Other objects of the invention will in part be obvious and will in part appear hereinafter. The invention accordingly comprises the apparatus possessing the construction, combination of elements, and arrangement of parts which are exemplified in the following detailed disclosure, and the scope of the application of which will be indicated in the claims.

For a fuller understanding of the nature and objects of the present invention, reference should be had to the following detailed description taken in connection with the accompanying drawings wherein.

The same numerals are used throughout the drawings to designate the same or similar parts.

Figure 1:
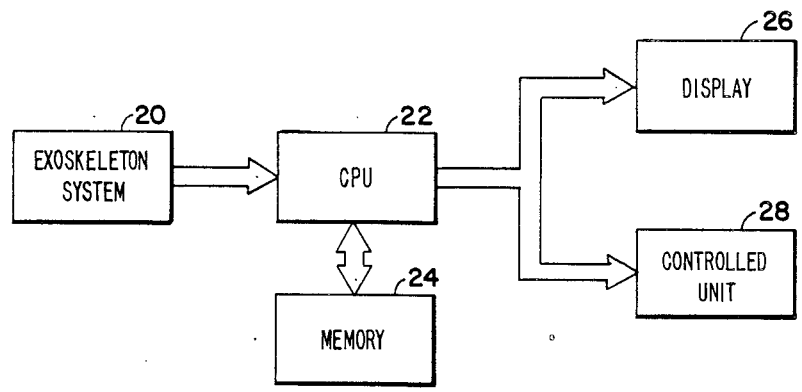
FIG. 1 is a block diagram of the preferred computerized system for obtaining and storing relative finger and thumb positions and movement of an operator's hand.

Referring to FIG. 1 the block diagram generally shows the preferred system including the exoskeletal unit 20, the latter being adapted to be supported on the operator's hand. The exoskeletal unit 20 preferably includes a plurality of sensors, one for each joint of the fingers of a hand for measuring the angle of each joint. Sensors are also provided for measuring the angle between any two fingers or between the index finger and thumb. Each sensor is used to provide an extremely accurate, high resolution output signal instantaneously representative of the actual relative angle of the corresponding finger or finger joint of the hand at any one instant of time.

All of the sensor outputs are transmitted to a control processor unit (CPU) 22 for processing the signals. As will more evident hereinafter, one function of the CPU 22 is to generate look up tables during an initial calibration procedure so that the angle sensed by each sensor (e.g., angle B in FIG. 3) can be quickly and accurately correlated with the actual angle of the corresponding joint or finger with which the sensor is being used (e.g., angle A in FIG. 3). Accordingly, memory 24 of suitable size is provided so as to store all of the calibration data generated during the initial calibration procedure.

Following the initial calibration procedure the output of the CPU 22 can be suitably connected to a display 26 for displaying data, and/or to a controlled unit 28, e.g., a robotic hand, whereby the exoskeletal unit 20 can be used to remotely control the controlled unit. It can also be connected to memory 24 to store the sensor signals which can be used as a measurement of the range of motion of the various joints of the fingers and thumb.

Figure 2:
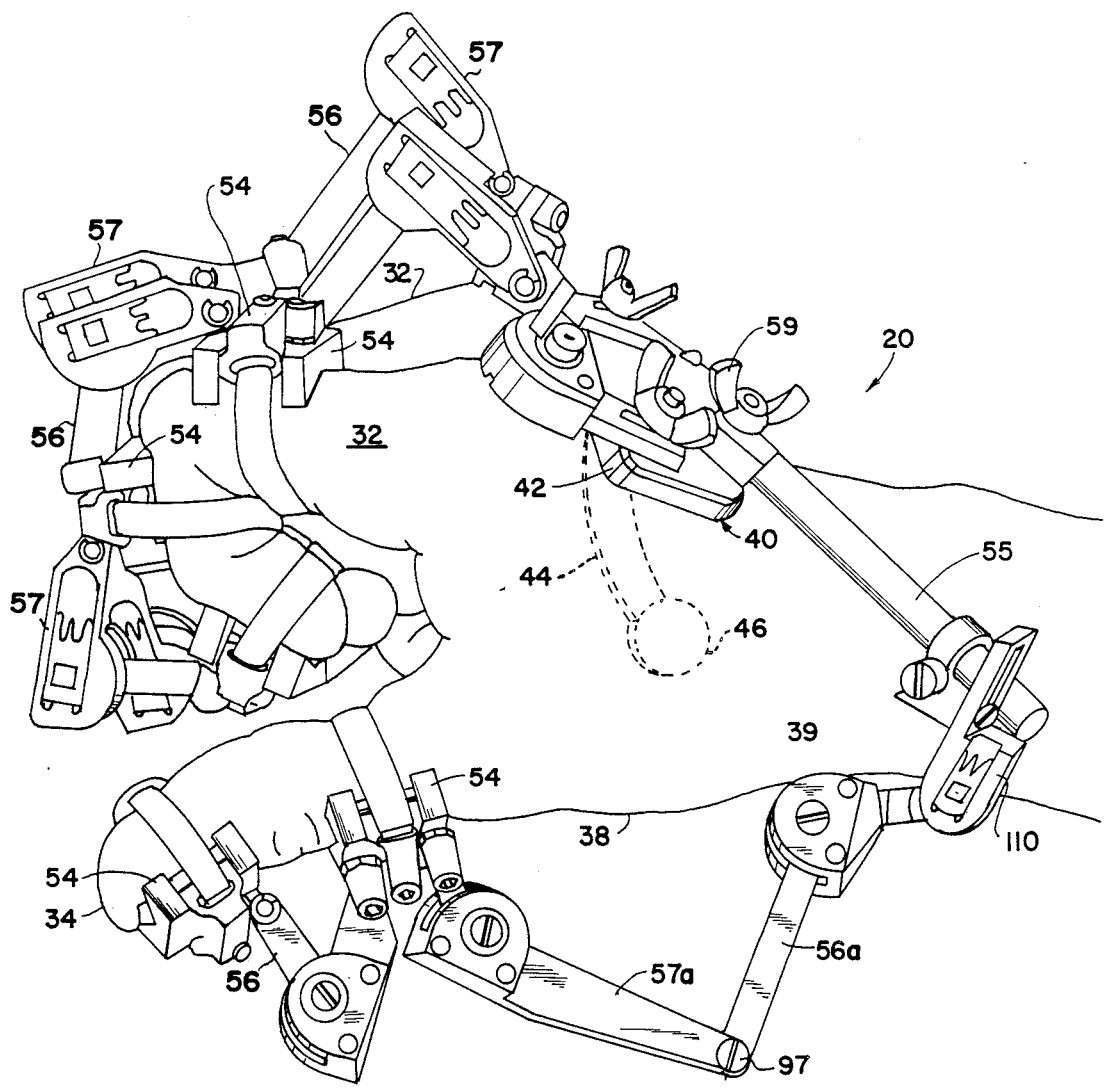
FIG. 2 is a perspective view of the preferred exoskeletal unit designed for use and shown on a human hand.

The preferred exoskeletal unit 20 is shown in FIG. 2, with details being shown in FIGS. 3–11. Unit 20 includes a hand clip 40 including a plate 42 and a spring clip (shown in phantom at 44). A button 46 secured to the end of the clip 44 is adapted to fit in the palm of the user's hand so that the clip 40 rests comfortably, yet tightly on the hand. The spring clip 44 is made of spring metal so that the hand clip comfortably fits on the hand 40 as shown, without moving relative to the hand.

A linkage assembly 52 for each finger 32 and thumb 34 is connected to the clip 40 and is adapted to be secured to the respective finger and thumb. Each linkage assembly includes two or three attachment assemblies 54, each adapted to be secured to a finger or thumb segment 36. Each linkage assembly 52 includes a plurality of links 56 and 57, or 56a and 57a supported by the clip 40 and attachment assemblies 54 so that a pair of links form a linkage pair 56 and 57, pivotally supported on opposite sides of each finger and thumb joint, and pivotally supported with respect to one another above the corresponding joint. For the thumb, one linkage pair 56a and 57a, with a sensor at each end to measure the angular displacement of each link independently, is interconnected by a passive pivot 97 with respect to the middle thumb joint (indicated at 38) and the proximal joint (indicated at 39) since an attachment assembly cannot be easily secured to the skeletal link provided between these two joints. The two sensors provide sufficient information to calculate the angles of the middle and proximal thumb joints even though no attachment is made to the segment connecting them. For the other joints means, coupled to each pair of links, are provided for sensing the relative angle between the two links, as will be more evident hereinafter, so that measurements can be made of the angles formed at the distal, middle and proximal joints of each finger and the distal joints of the thumb.

Figure 6:
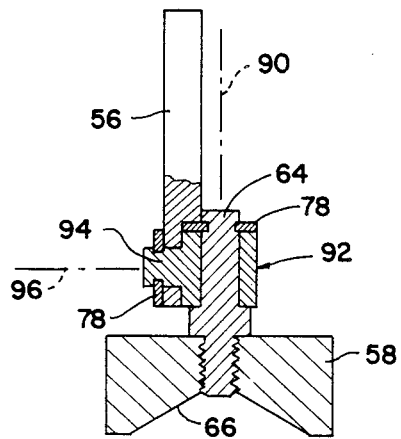
FIG. 6 is a cross-sectional view taken along line 6—6 of FIG. 5.
Figure 7:
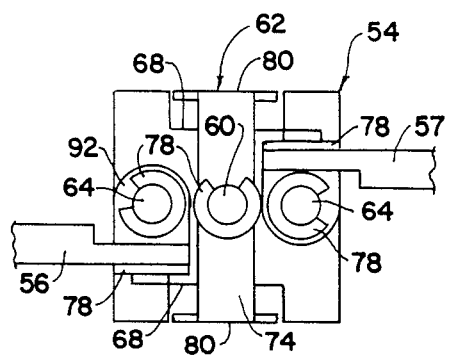
FIG. 7 is a top view of the finger base assembly of FIG. 5.
Figure 8:
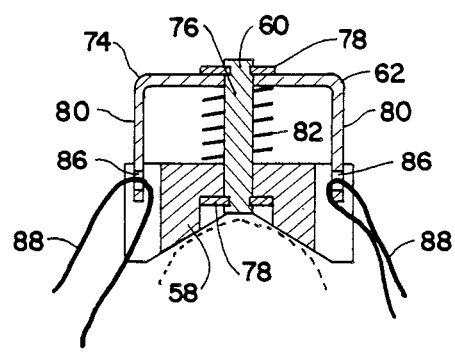
FIG. 8 is a cross-sectional view taken along line 8—8 of FIG. 5.

Referring to FIGS. 5–8 each attachment assembly 54 includes an attachment base 58, a strap post 60, a strap mount 62 and at least one pivot post 64 (the assembly 54 adapted to be secured to the distal end segment of each finger and thumb is provided with one pivot post, while the other assemblies are provided with two posts). As shown in FIGS. 6 and 8, the bottom of attachment base 58 is formed with a groove 66 of triangular cross-section adapted to align with and receive the portion of the finger or thumb segment to which the base member is secured. The triangular cross-section provides a stable base which accommodates fingers of different sizes thereby avoiding the problems of earlier designs. The attachment base also includes a side groove 68 (see FIGS. 5, 7 and 8) formed on each side of the attachment base. An aperture is formed in the center of the base member from the top surface to the bottom groove 66 for receiving the strap post 60 (see FIG. 8). Preferably, the post 60 is maintained in place by snap rings 78 adapted to fit into grooves provided at both ends of the post.

The strap mount 62 is a U-shaped bracket including intermediate portion 74 formed with a hole. The hole is large enough to freely receive the shaft of the strap post 60 but smaller than the snap ring 78 so that the mount will be retained by the snap ring when the mount is positioned on the base assembly. The side portions 80 of the strap mount 62 are adapted to fit within the side grooves 68 so that the mount is slidable in a vertical direction between the two pivot posts 64. Suitable bias means, preferably in the form of a compression spring 82 (see FIG. 8), biases the strap mount from the attachment base 58. This mounting accommodates changes in finger diameters as they are flexed by allowing motion in one direction only thereby providing a significantly more stable mounting than provided by an elastic strap which can stretch in any direction. The side portions 80 of the strap mount 62, each includes a slot 86 for receiving a strap 88. The strap 88 is sufficiently long and is provided with suitable fastening means, such as the material manufactured under the trademark VELCRO, so that the strap can be secured through one slot, tightly wrapped around the finger or thumb segment, threaded through the other slot, and secured to itself so as to maintain the attachment assembly 54 in a secure and stable position on the finger or thumb segment.

The two pivot posts 64 are secured in the attachment base 58 on opposite sides of the strap mount 62 so that the vertical axes 90 of the posts are substantially parallel to one another (see FIG. 6). A cylindrical element 92 is pivotally mounted on each post 64 so as to pivot about the corresponding axis 90, while being suitably restrained from axial movement with a snap ring 78. Each cylindrical element 92 includes a shaft portion 94 so that the axis 96 of the shaft portion is perpendicular to the vertical axis 90 of the corresponding post to which the cylindrical element is pivotally secured. One end of a link 56 or 57 is secured to the shaft portion 94 so that the link can pivot about the axis 96 and pivot with the cylindrical element 92 about the axis 90.

All of the parts for the base assembly and links are preferably made of a non-magnetic material, such as anodized aluminum, non-magnetic stainless steel and plastic.

Figure 3:
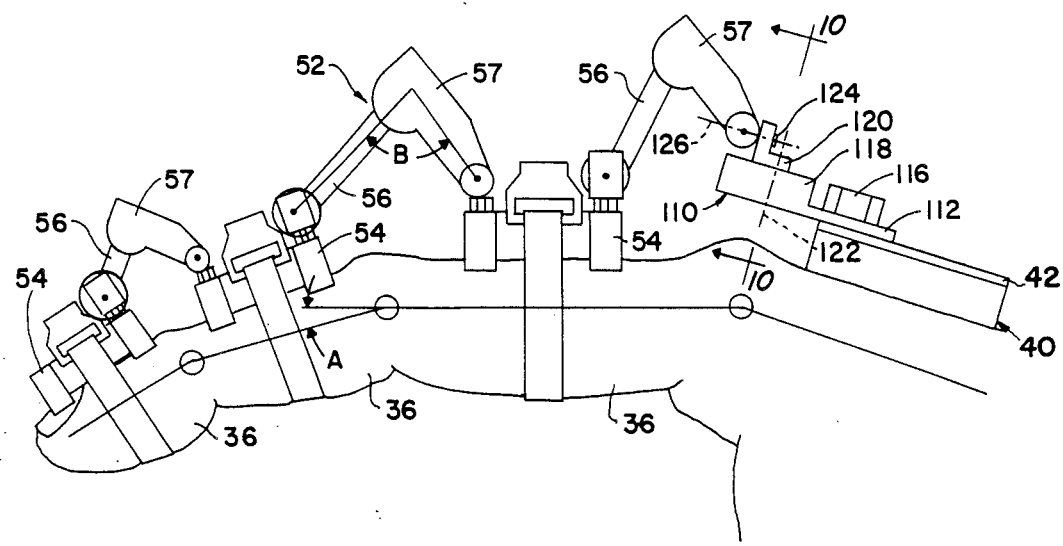
FIG. 3 is a side view of the portion of the exoskeletal unit of FIG. 2 attached to a finger.
Figure 4:
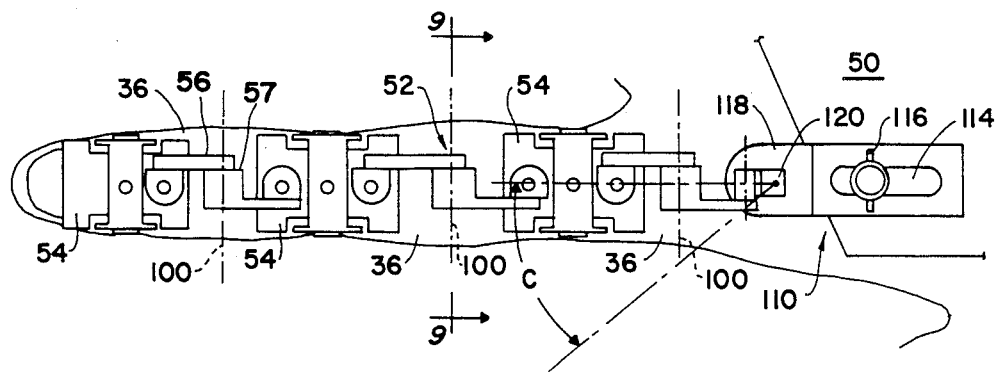
FIG. 4 is a top view of the portion of the exoskeletal unit of FIG. 2 attached to a finger.
Figure 5:
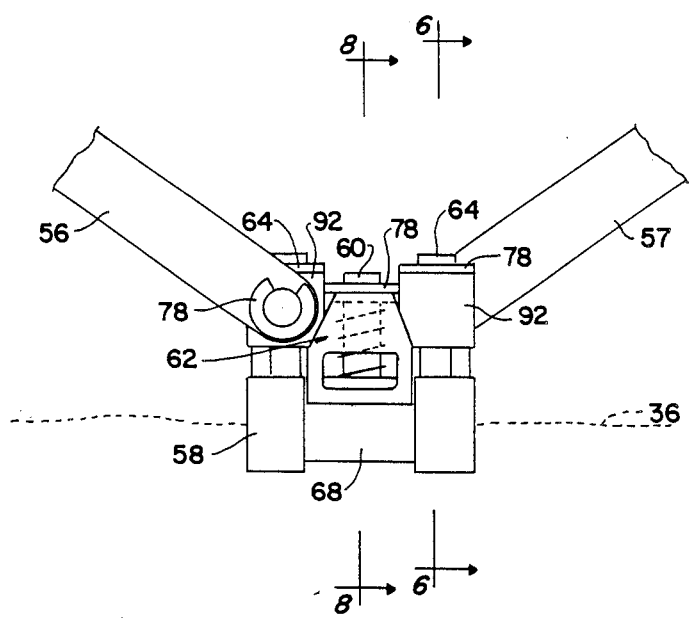
FIG. 5 is a side view, with a portion cut away, of one finger base assembly of the exoskeletal unit of FIG. 2.

As shown in FIGS. 2-4, the attachment assemblies 54 on the distal ends of the thumb and fingers include only a single pivot post 64 with an identical cylindrical element and pivot pin 94 so that the link connected to the attachment assembly pivots about a corresponding axis 90 and 96.

Figure 9:
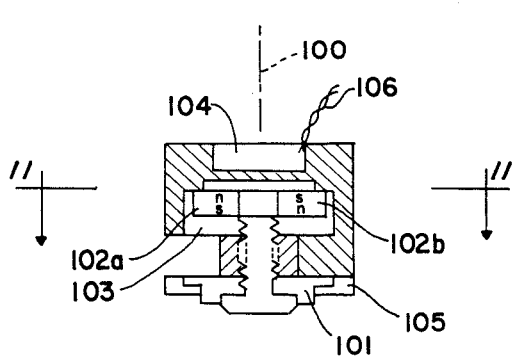
FIG. 9 is a cross-sectional view taken along line 9—9 of FIG. 4.
Figure 11:
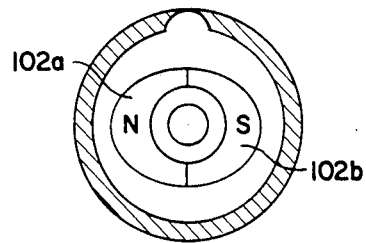
FIG. 11 is a cross-sectional view taken along line 11—11 of FIG. 9.

Referring to FIG. 2, the linkage used to measure the angle of the middle joint 38 and proximal joint 39 of the thumb includes two linkage pairs secured about a passive pivot 97 since the unit cannot be easily secured to the skeletal link segment of the hand between the middle and proximal joints 38 and 39. One linkage pair is accordingly secured to the attachment assembly 54 attached between the distal thumb joint and middle thumb joint 38, while the other linkage pair is secured to an assembly 110 (described in greater detail hereinafter), which in turn is adjustably secured to the support rod 55 so that the assembly can be properly positioned relative to the proximal joint 39. Rod 55 is in turn secured to the plate 42 of the clip 40 by any suitable means such as bolt and wing nut 59. As shown in FIGS. 4 and 9, each linkage pair, formed by the links 56 and 57, is pivotally secured together about a pivot axis 100 by any suitable means (such as bearing elements 101, 103 and cap 105 as shown best in FIG. 9). Each linkage pair is provided with magnetic means preferably in the form of two magnets 102a and 102b secured at the end of the link 56, and a Hall effect sensor 104, secured the link 57, for accurately detecting the relative angular position of the two links about the pivot axis 100. Each sensor is provided with output leads 106. As is well known, the sensor will generate an electrical signal as a function of the strength of the magnetic field sensed by the sensor. As best shown in FIGS. 9 and 11, the two magnets are "horseshoe" in shape and are positioned in link 56 on opposite sides of the pivot axis 100. The magnets are identical to one another with the poles of the magnets being axially spaced from one another, except that the polarity orientation of one magnet is the opposite of the polarity orientation of the other magnet so that the sensor is disposed a predetermined distance from the south pole of one magnet and the north pole of the other magnet. The magnet assemblies are custom made and purchased from Sarcos, Inc. of Salt Lake, UT. The magnets are shaped so that the magnetic field sensed by the Hall effect sensor 104 varies 360° around the pivot axis. Thus, the amplitude of the output signal of sensor 104 will vary as a function of the relative angular orientation of the two links. Sensors manufactured by the Microswitch division of Honeywell Corporation under model SS9 Series may be used. Such sensors when used with the magnets 102a and 102b will provide a substantially linear output signal as a function of angle over a 180° range with +/−0.1° accuracy.

Figure 10:
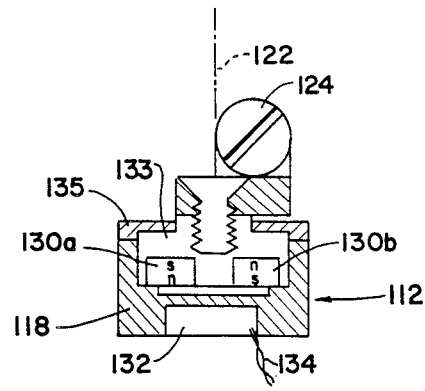
FIG. 10 is a cross-sectional view taken along line 10—10 of FIG. 3.

As shown in FIGS. 3, 4 and 10, assembly 110 for securing a link to the plate 42 of clip 40 is different from the attachment assembly 54. Assembly 110 includes a plate member 112 including a slot 114 (see FIG. 4) for securing the assembly to the clip 40 with suitable means such as a wing nut and bolt 116. Plate member 112 includes a sensor holder portion 118 for supporting the pivot member 120 so that the pivot member is pivotable about and axially restrained with respect to the pivot axis 122. A pivot pin 124 is secured to the member 120 with the axis 126 of the pin substantially perpendicular to the axis 122 (see FIG. 3). One end of a link 57 is secured to the pivot pin 124 so that the link can pivot about the axis 126 and pivot with the pivot member 120 about the pivot axis 122.

As shown in FIG. 10, magnetic means are also provided at each pivot axis 122, for accurately detecting the relative angular position between adjacent fingers and/or thumb. As best seen in FIG. 10, the magnetic means employed at the axis 122 also preferably includes two horse shoe magnets 130a and 130b and a Hall effect sensor 132 disposed in a relatively horizontal orientation so that the magnetic field sensed by the sensor varies as the link assembly is moved about the axis 122. The sensor includes leads 134. The two magnets are positioned in a bearing 133 and held in place by cap 135, while the sensor is positioned in the sensor holder portion 118, opposite the magnets so as to be arranged relative to one another in an identical manner as the two magnets and sensor positioned in each pair of pivotable links 56 and 57. The two magnets 130a and 130b and sensor 132 may be the same type of available devices used for magnets 102a and 102b and sensor 104. Accordingly, the sensor 132 operates identically to the sensor 104 in sensing the magnetic field provided by the magnets.

In use the unit 20 is attached by securing the clip 40 over the hand. The individual linkage assemblies 52 are attached to the corresponding fingers and thumb by securing each attachment assembly 54 to the respective finger and thumb segment so that a pair of links 56, 57 are connected to each finger and thumb skeletal link segment. In attaching each attachment base 58, the bottom groove 66 is positioned on the finger or thumb skeletal link segment and the strap 88 is wrapped around the finger or thumb segment and tightened so that each attachment assembly will not move relative to the finger or thumb to which it is attached as the finger or thumb is moved. The spring bias provided by the compression spring 82 allows movement of the attachment base 58 relative to the strap mount 62 in order to accommodate changes in the cross-section of the finger or thumb segment as the finger or thumb is bent about the joint whose angle is being measured while preventing relative movement between the linkage assembly and the finger or thumb so as to substantially prevent any motion artifacts being introduced.

When properly positioned, the pivot axis 100 of each linkage pair 56 and 57 will be positioned substantially above (but not necessarily directly above), as opposed to the side of, each joint as the joint is bent, and oriented substantially parallel to the pivot axis of the joint so that as the joint is bent and straightened the angle between each pair of links will vary. Different hand sizes can easily be accommodated by adjusting the straps 88 and releasing wing nuts 116 and moving the assembly 110 relative to the plate 42. To adjust the thumb mechanism the linkage can be slid along rod 55 and the assembly tightened in position. When properly positioned each assembly 110 will be positioned directly over either a knuckle or the proximal thumb joint 39 with the pivot axis 122 passing through the corresponding proximal joint so that each sensor 132 will sense the relative angular position of the respective finger and thumb, i.e., the radial/ulnar deviation (angle C in FIG. 4).

Further, as will be evident hereinafter, the fact that the angular motion provided between each pair of links 56 may vary for the same joint angle as a function of (1) which joint is being monitored, (i.e., the correlated movement of the angle of the joint of the finger or thumb with the movement of the corresponding angle of the pair of links may be different, for example, for a proximal joint than for a distal joint of a finger or thumb), and (2) the size of the user's hand (including the length of the fingers and thumb), will be taken into account so that these variables are substantially irrelevant.

It should be appreciated that once exoskeletal unit 20 is secured to the hand the pivoting action provided about the pivot axes 90, 96, 100, 122 and 126 allows the unit to follow the movement of the hand, and minimizes any movement between the exoskeletal unit and the hand which otherwise might result from forces being placed on the exoskeletal unit where the unit might not necessary be adapted to follow the movement of the hand as in the prior art developed by Sarcos, Inc., described above.

Figure 12:
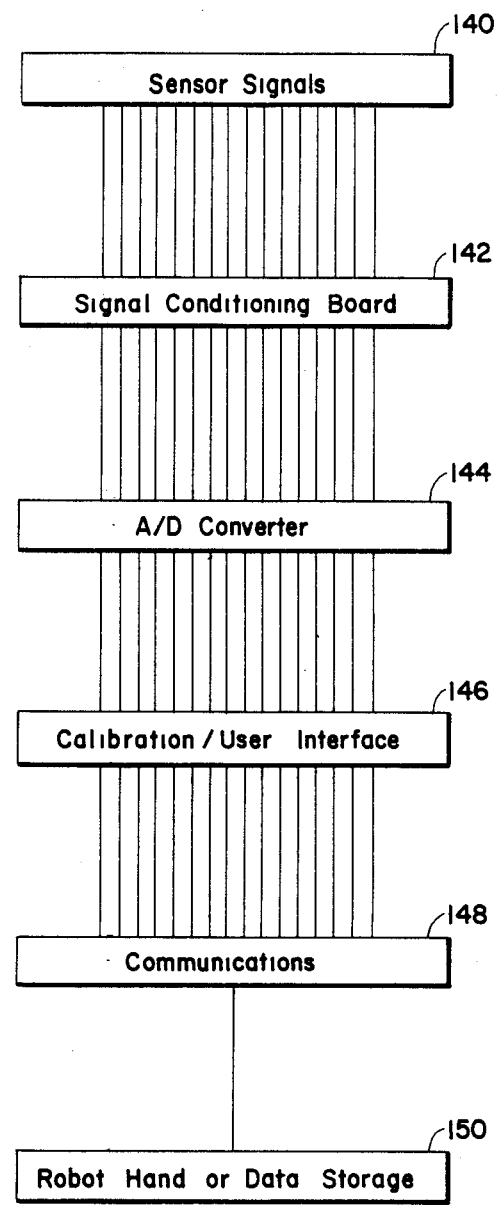
FIG. 12 is a block diagram of the flow chart of the control processor unit of FIG. 1.

All of the sensors 104 (fifteen sensors in all, with one sensor for each finger and thumb joint) and all of the sensors 132 (five sensors in all, with one sensor for each finger and the thumb) are suitably connected through the leads 106 and 134 to a the CPU 22 positioned near the user. Connection is made through low resistance wiring (not shown) such that the CPU is capable of distinguishing each signal and identifying the signal with the particular sensor generating the signal. The output of the sensors 104 and 132 are sampled at a relatively rapid rate, e.g. 100 Hz. As shown in FIG. 12 the sensor signals provided over the wiring, as indicated at 140, will be transmitted to a suitable conditioning board for conditioning the signal (such as amplifying the signal) as indicated at 142. The conditioned signals are converted to digital signals as indicated at 144 and transmitted to a calibration/interface 146. Following calibration, information can be communicated as indicated at 148 to the controlled unit 28 or to data storage 24, as indicated at 150.

In accordance with one aspect of the present invention, measurements provided by each of the sensors 104 and 132 can be initially calibrated by the user before the unit 20 is employed to generate signals representative of various hand positions, so as to take into account the particular user's hand size and the particular joint each sensor is measuring. This calibration can be accomplished in one of at least two ways.

A first calibration technique requires the user to physically take measurements of positions of the hand. The length is measured (a) of each skeletal link segment of the fingers and thumb, including the length between the proximal thumb joint and the middle thumb joint, and (b) between each of the finger and thumb link center lines (the longitudinal axis through the bone of each finger and thumb links) and a predetermined part of the exoskeletal unit, such as the corresponding attachment base 58 secured to the finger and thumb link. This data is manually entered by the user into the memory 24 through the CPU 22. In addition, the memory 24 is preprogrammed to contain a geometric representation of the exoskeletal system defining linkage lengths and the angular relationships of the parts. The relationship between the sensor values and linkage angles is also stored, thus a look up table using these data to relate sensor readings to human joint angles can be created. This completes the calibration.

In accordance with another calibration technique, the user need not make the initial measurements of the length (a) of each skeletal link segment of the fingers and thumb, and (b) between each of the finger and thumb link center lines (the longitudinal axis through the bone of each finger and thumb links) and a predetermined part of the exoskeletal unit, such as the corresponding attachment base 58 secured to the finger and thumb link. Instead the user places objects of various shapes and dimensions in his or her hand and the various angles sensed by each sensor 104 are read by the CPU and stored in memory. For example, the hand can be placed against a flat surface and the angles read. Cylinders of predetermined radii can then be held in the user's hand and the angles sensed by the sensors 104 read for each cylinder. Other such objects can also be used. The use of the objects is designed to provide sufficient information so that each look up table for each respective sensor 104 can be generated. Using the information about the geometry of each linkage assembly 52 and the sensor data, a set of simultaneous equations are created and solved for the lengths and the relationships between the linkage angles and finger link angles.

It should be appreciated that in either event, each sensor 132, once calibrated, will sense the actual lateral angle provided between the fingers and thumb since the sensors 132 are above the corresponding proximal finger and thumb joint with the respective pivot axis 122 extending though the joint.

The system thus described provides measurement of the angular orientation of two joint segments forming a joint with improved accuracy and greater resolution than achieved by the prior art previously described. Generally, the magnets and Hall effect sensor used to measure each angle provide a clean and more accurate measurement of the angle measured by each than heretofore achieved by potentiometers used in the prior art. By securely fastening the attachment assemblies 52 and allowing the linkage to pivot about the axes 90, 96, 100, 122 and 126 errors attributed to motion artifacts will be minimized since the motion of the attachment assemblies 52 and clip 50 relative to the hand will be minimized, even though a finger or thumb may be crooked and the bending action of the fingers and thumb causes out of plane rotation of the various links. The pivoting action about the pivot axes 90, 96, 100, 122 and 126, as well as the light weight of the whole sensor unit 20, provides a much lighter weight and more flexible unit than the systems of the prior art. Further, the construction of the exoskeletal unit and the ability to calibrate the exoskeletal unit, permits the exoskeletal unit to be used with many different sized hands.

Since certain changes may be made in the above apparatus without departing from the scope of the invention herein involved, it is intended that all matter contained in the above description or shown in the accompanying drawing shall be interpreted in an illustrative and not in a limiting sense.

What is claimed is:

1. A system for use in sensing the relative angular orientation of at least two movable adjacent skeletal link segments of a living body joined together at a joint, said system comprising:
   first and second links coupled together about a first pivot axis so that said links are pivotable relative to one another about said axis so as to define a variable angle between said links about said first pivot axis;
   securing means for securing said first and second links relative to said skeletal link segments so that said links pivot about said first pivot axis when said skeletal link segments pivot about said joint, wherein said securing means includes an attachment assembly for attaching said links to each of said skeletal link segments so that said links pivot relative to said attachment assembly about two degrees of freedom and follow the relative angular movement of the skeletal link segments with reduced artifacts due to motion between said attachment assembly and said skeletal link segments; and
   sensor means for sensing said angle between said skeletal link segments.

2. A system according to claim 1, wherein said attachment assembly includes means for attaching said link so that said link is pivotable about second and third, mutually perpendicular pivot axes relative to said attachment assembly with reduced artifacts due to motion between said attachment assembly and said skeletal link segments.

3. A system according to claim 1, wherein said sensor means includes a Hall effect sensor.

4. A system according to claim 1, wherein said attachment assembly includes means for accommodating changes in the cross-section of each skeletal link segment as the adjacent skeletal link segments are bent about the joint, while preventing relative movement between said skeletal link segments and said attachment assembly so as to substantially reduce artifacts due to motion between said attachment assembly and said skeletal link segments.

5. A system according to claim 1, further including means for correlating the angle sensed by said sensor means with said angular orientation made by said adjacent skeletal link segments.

6. A system according to claim 1, wherein said means for securing said first and second links secures said links so that said first pivot axis is displaced from and substantially parallel to the pivot axis of said joint.

7. A system according to claim 5, wherein said links are adapted to be positioned so that said first pivot axis is above the pivot axis of said joint.

8. A system according to claim 5, wherein said means for correlating said angle between said links with the angle made by said skeletal link segments includes means comprising a lookup table containing the correlation between said angle between said links, and the angle between said skeletal link segments.

9. A system according to claim 5, wherein said means for correlating said angle between said links with the angle made by said skeletal link segments includes means containing a set of simultaneous equations for determining the correlation between said angle between said links and the angular orientation made by said skeletal link segments.

10. A system for use in sensing the relative angular orientation of the fingers and thumb of a hand, said system comprising:
   (A) an exoskeletal unit adapted to be secured to said hand, said exoskeletal unit comprising:
      (a) a plurality of pairs of links, each pair for use with a corresponding joint of the fingers and thumb, the links of each pair being coupled together so that said links of each pair are pivotable relative to one another about a first pivot axis so as to define a variable angle between said links of said pair about said axis;
      (b) securing means for securing said pairs of links to said hand so that each pair of links is secured relative to the adjacent skeletal link segments of the fingers and thumb of said hand joined at the corresponding joint with which said pair of links is used so that said pair of links pivot about said pivot axis when said adjacent skeletal link segments pivot about said joint, wherein said securing means includes an attachment assembly for attaching said links to each of said skeletal link segments so that said links pivot relative to said attachment assembly about two degrees of freedom and follow the relative angular movement of the skeletal link segments with reduced artifacts due to motion between said attachment assembly and said skeletal link segments; and
      (c) sensor means, secured to each pair of links, for sensing said angle between said links; and
   (B) means for correlating the angle sensed by said sensor means with the angle made by the corresponding adjacent skeletal link segments.

11. A system according to claim 10, wherein said sensor means includes a Hall effect sensor.

12. A system according to claim 10, wherein said means for correlating said angle sensed by said sensor means with the angle made by said skeletal link segments includes means comprising a lookup table containing the correlation between said angle sensed by said sensor and the angle made by said corresponding adjacent skeletal link segments.

13. A system according to claim 10, further including means for sensing the relative angular position of each of said fingers and thumb relative to one another.

14. A system according to claim 10, wherein said securing means includes a plurality of attachment assemblies for attachment to corresponding ones of said skeletal link segments, wherein each of said attachment assemblies includes means for accommodating changes in the cross-section of each skeletal link segment as the adjacent segments are bent about the joint, while preventing relative movement between said skeletal link segments and said attachment assembly so as to reduce artifacts due to motion between said attachment assembly and said skeletal link segments.

15. A system for use in sensing the relative angular orientation of two movable adjacent skeletal link segments of a living body joined together at a joint, said system comprising:
first and second links;
attachment assembly means for coupling said links relative to said adjacent skeletal link segments so that said links are movable relative to one another as said skeletal link segments move relative to one another as said skeletal link segments move relative to one another wherein said attachment assembly means cooperates with said links and said adjacent skeletal link segments so that artifacts due to motion between said attachment assembly means and said skeletal link segments are reduced;
signal generating means, responsive to the relative position of said links, for generating a sensor signal representative of the relative angular orientation of said links;
means for storing data regarding the physical features of said skeletal link segments; and
means for generating a finger angle signal representing the angular orientation of said joint as a function of said sensor signal and said stored data.

16. In a system for use in sensing the relative angular orientation of two movable adjacent skeletal link segments of a living body joined together at a joint, said system comprising: (a) first and second links coupled together about a pivot axis so that said links are pivotable relative to one another about said axis so as to define a variable angle between said links about said axis; (b) securing means for securing said links with respect to said skeletal link segments so that said links pivot about said pivot axis when said skeletal link segments pivot about said joint; (c) sensor means, secured to said first and second links, for sensing said angle between said segments; and (d) means for correlating the angle sensed by said sensor means with said angular orientation made by said skeletal link segments; wherein the improvement comprises:
said securing means including an attachment assembly for securing said each of said links relative to the corresponding skeletal link segment, each said attachment assembly including means for accommodating changes in the cross-section of said corresponding skeletal link segment as the skeletal link segments are bent about the joint, while preventing relative movement between said one skeletal link segment and said attachment assembly.

17. The system according to claim 16, wherein each said attachment assembly includes (a) an attachment base, (b) a post fixed to said base, (c) a strap mount slidably mounted on said post relative to said base, (d) means for biasing said strap mount away from said base, and (e) a strap, secured to said strap mount and adapted to be secured around said one skeletal link segment, for securing said assembly to the corresponding skeletal link segment, wherein said mount and base move relative to one another as the cross-section of said corresponding skeletal link segment varies.

18. The system according to claim 16, wherein said base includes a groove shaped to engage the surface of said corresponding skeletal link segment.

19. The system according to claim 18, wherein said groove is V-shaped.

20. In a system for use in sensing the relative angular orientation of two movable adjacent skeletal link segments of a living body joined together at a joint, said system comprising: (a) first and second links coupled together about a pivot axis so that said links are pivotable relative to one another about said axis so as to define a variable angle between said links about said axis; (b) securing means for securing said links with respect to said skeletal link segments so that said links pivot about said pivot axis when said skeletal link segments pivot about said joint; (c) sensor means, secured to said first and second links, for sensing said angle between said segments; and (d) means for correlating the angle sensed by said sensor means with said angular orientation made by said skeletal link segments; wherein the improvement comprises:
said securing means including an attachment assembly for securing each of said links relative to a corresponding one of said skeletal link segments, each said attachment assembly including means for pivotally attaching a corresponding link to said attachment assembly relative to two degrees of freedom so as to reduce artifacts due to motion between said link and said corresponding one of said skeletal link segments.

21. In a system for use in sensing the relative angular orientation of the skeletal link segments forming the proximal and distal joints of the thumb of a hand, said system comprising:
first, second, third and fourth links coupled together so that (a) said first and second links are pivotal relative to one another about a first axis so as to define a first variable angle, (b) said second and third links are pivotal relative to one another about a second axis, and (c) said third and fourth links are pivotal relative to one another about a third axis so as to define a second variable angle;
means for securing said firs, second, third and fourth links with respect to said skeletal link segments so that said links pivot about said pivot axes when said skeletal link segments pivot about said joints;
sensor means, secured to said first and second links and to said third and fourth links, for sensing said first and second variable angles; and
means for correlating the angles sensed by said sensor means with said angular orientation made by said skeletal link segments.

22. The system according to claim 21, wherein said means for securing said first, second, third and fourth link segments includes means for securing said first and fourth link segments relative to said hand.

* * * * *

UNITED STATES PATENT AND TRADEMARK OFFICE
CERTIFICATE OF CORRECTION

PATENT NO. : 4,986,280
DATED : January 22, 1991
INVENTOR(S) : Beth Marcus, W. Thompson Lawrence and Philip Churchill It is certified that error appears in the above-identified patent and that said Letters Patent is hereby corrected as shown below:

Column 11;

Claim 15, lines 28-29, delete "as said skeletal link segments move relative to one another"; and Column 12;
   Claim 21, line 54, delete "firs" and insert therefor -- first --.

Signed and Sealed this

Seventh Day of July, 1992

Attest:

DOUGLAS B. COMER

Attesting Officer

Acting Commissioner of Patents and Trademarks